United States Patent [19]

Asnis et al.

[11] Patent Number: 5,217,462
[45] Date of Patent: Jun. 8, 1993

[54] SCREW AND DRIVER

[75] Inventors: Stanley E. Asnis, Port Washington, N.Y.; John S. Crombie, Irvington, N.J.; Lewis B. Lane, Manhasset, N.Y.

[73] Assignee: Pfizer Hospital Products Group, Inc., New York, N.Y.

[21] Appl. No.: 664,905

[22] Filed: Mar. 5, 1991

[51] Int. Cl.⁵ .............................................. A61B 17/00
[52] U.S. Cl. ......................................... 606/73; 606/72; 606/105
[58] Field of Search .................. 606/53, 60, 62, 65, 606/66, 72, 73, 105; 81/439, 440

[56] References Cited

U.S. PATENT DOCUMENTS

| | | | |
|---|---|---|---|
| 4,262,665 | 4/1981 | Roalstad et al. | 606/62 |
| 4,328,721 | 5/1982 | Massari | 81/439 |
| 4,456,005 | 6/1984 | Lichty | 606/60 |
| 4,640,271 | 2/1987 | Lower | 606/65 |
| 4,858,601 | 4/1989 | Glisson | 606/65 X |
| 4,867,018 | 9/1989 | Spector | 81/439 |
| 4,919,679 | 4/1990 | Averill et al. | 606/62 X |
| 4,940,467 | 7/1990 | Tronzo | 606/65 X |
| 4,963,144 | 10/1990 | Huene | 606/72 X |

OTHER PUBLICATIONS

Richars Manufacturing Co., Advertisement, May 1949.

*Primary Examiner*—Robert A. Hafer
*Assistant Examiner*—Sam Rimell
*Attorney, Agent, or Firm*—Peter C. Richardson; Lawrence C. Akers; Elizabeth O. Slade

[57] ABSTRACT

An implant comprising a specially adapted bone screw having a threaded shank portion and a sleeve which mates with and operates in cooperation with the threaded shank portion is provided. Also provided is a driver specially adapted for inserting and removing the implant of the invention. A method of compressing a fracture in a bone is also provided. The implant generates bone compression by itself and can be used either alone or with plates and washers. It is easily inserted into a fracture and also is easily removed from the fracture. The driver which is specially adapted to be used in combination with the implant of the invention aids in the ease of insertion and removal of the implant.

6 Claims, 4 Drawing Sheets

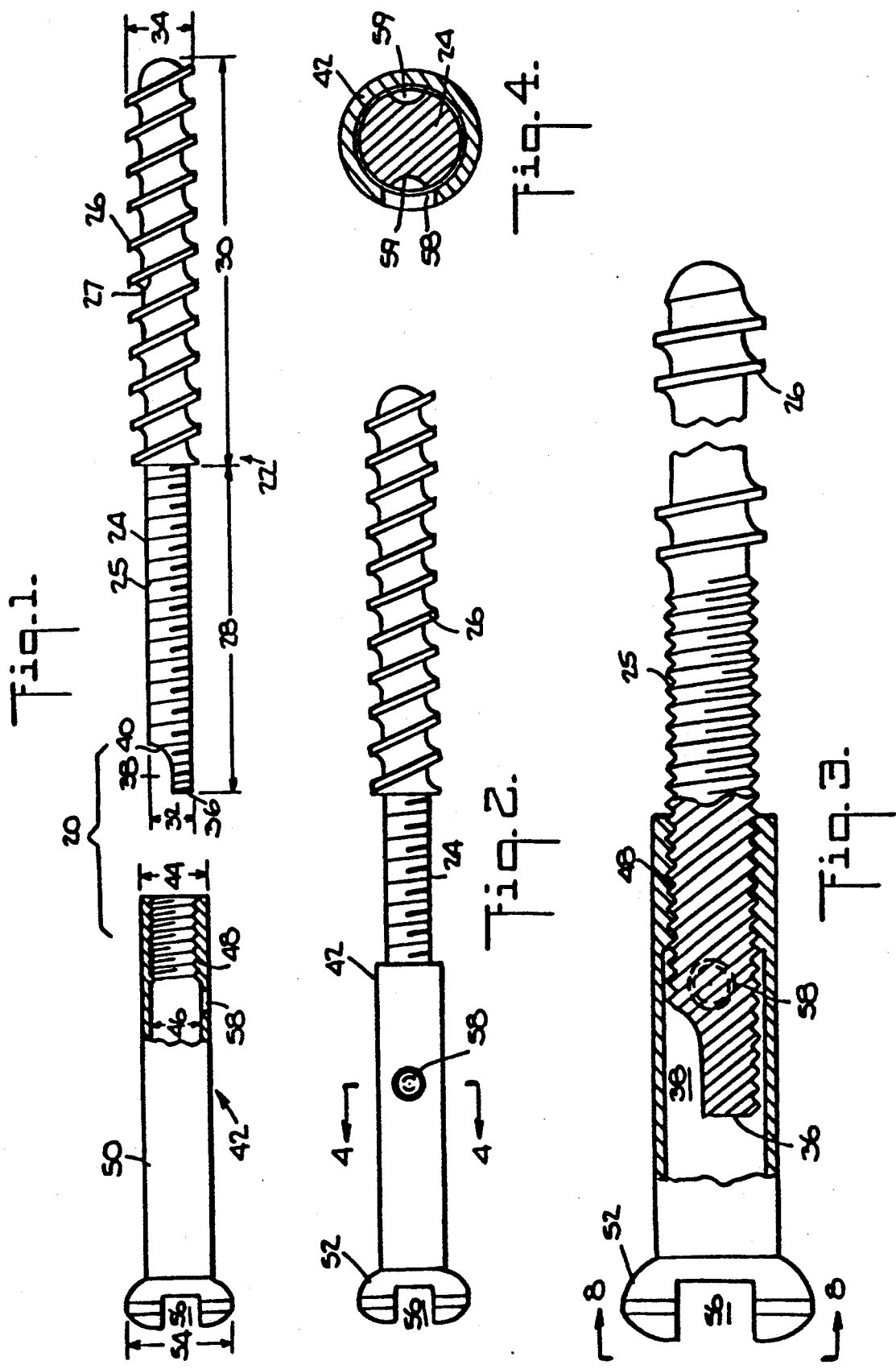

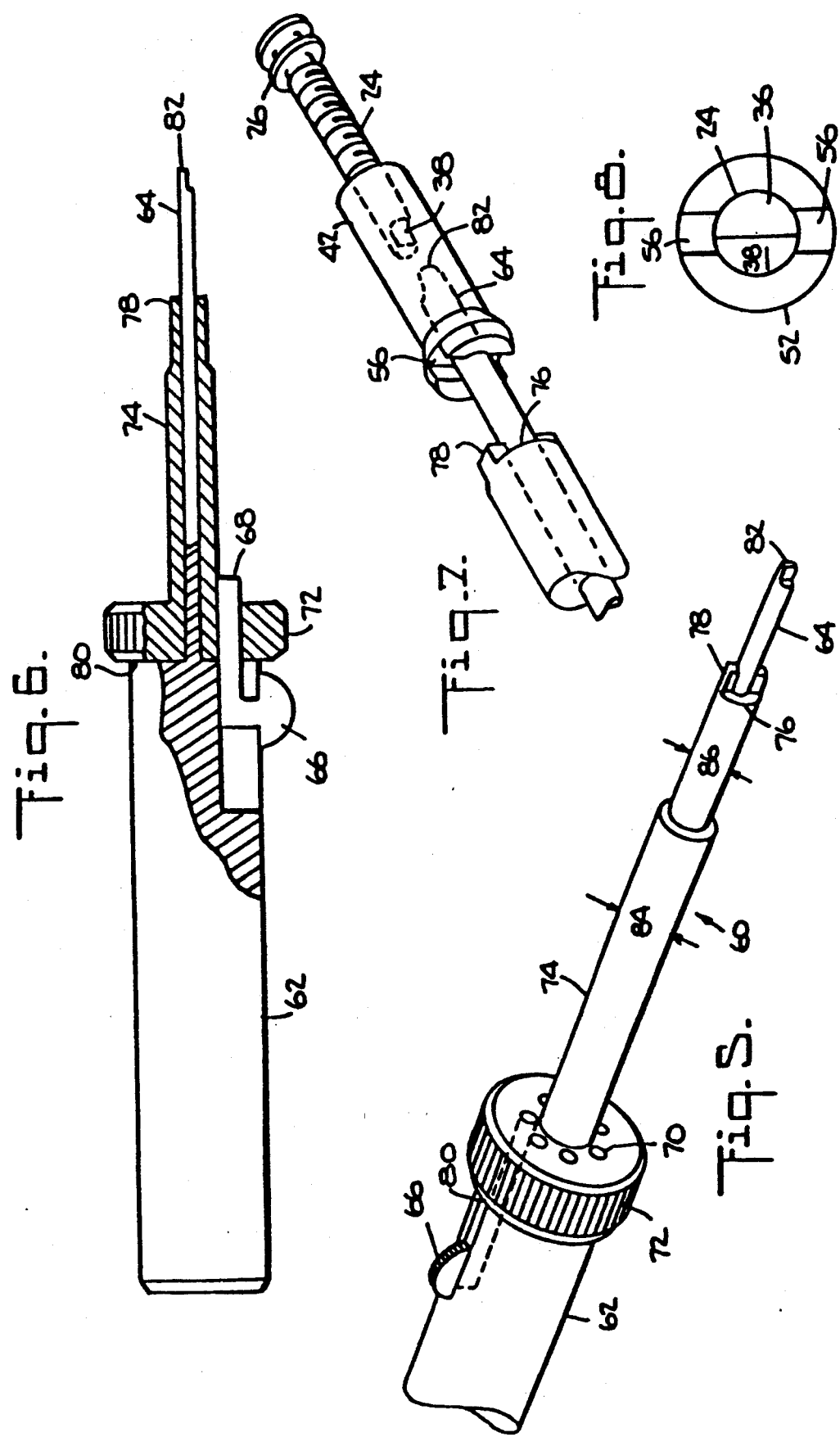

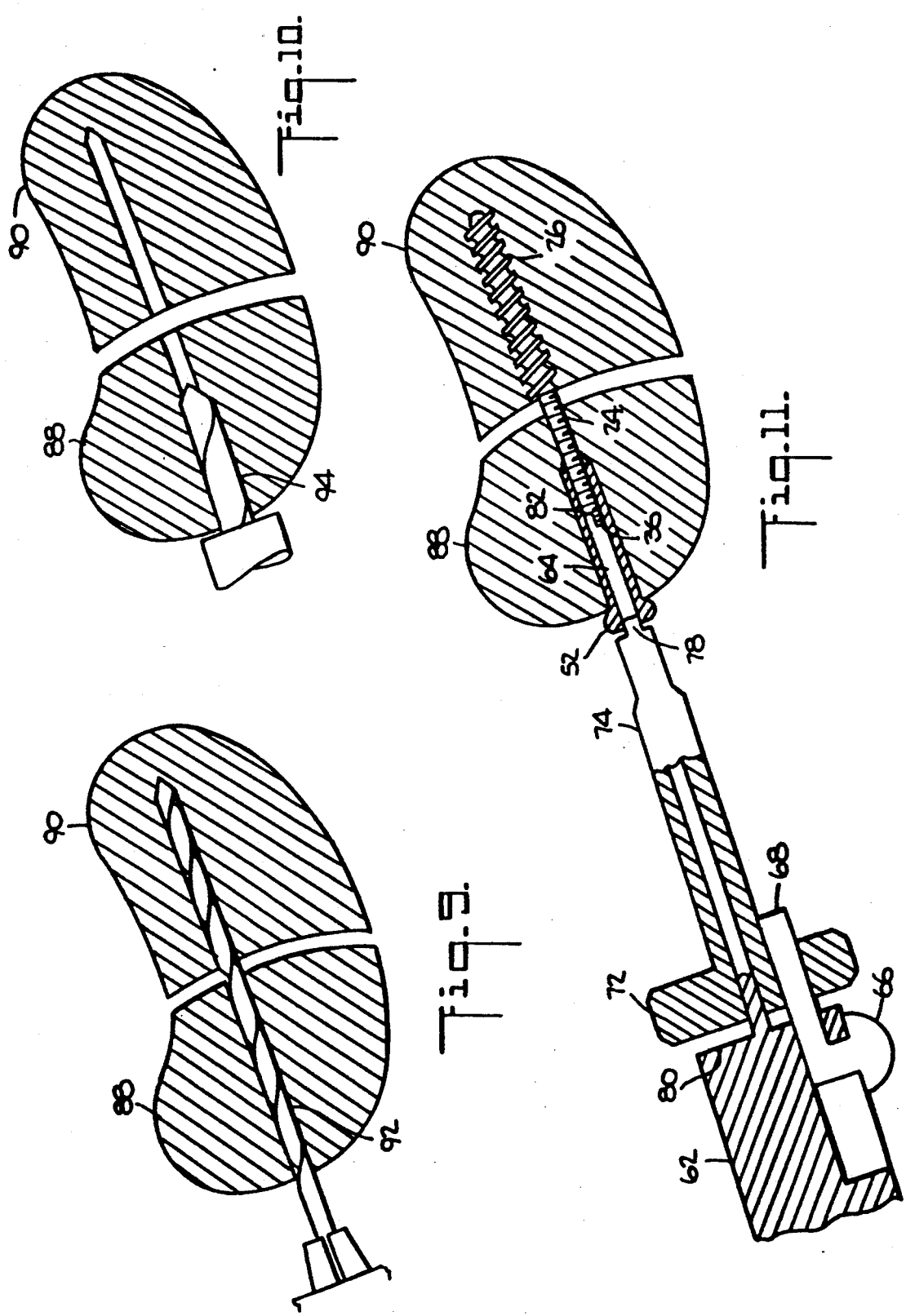

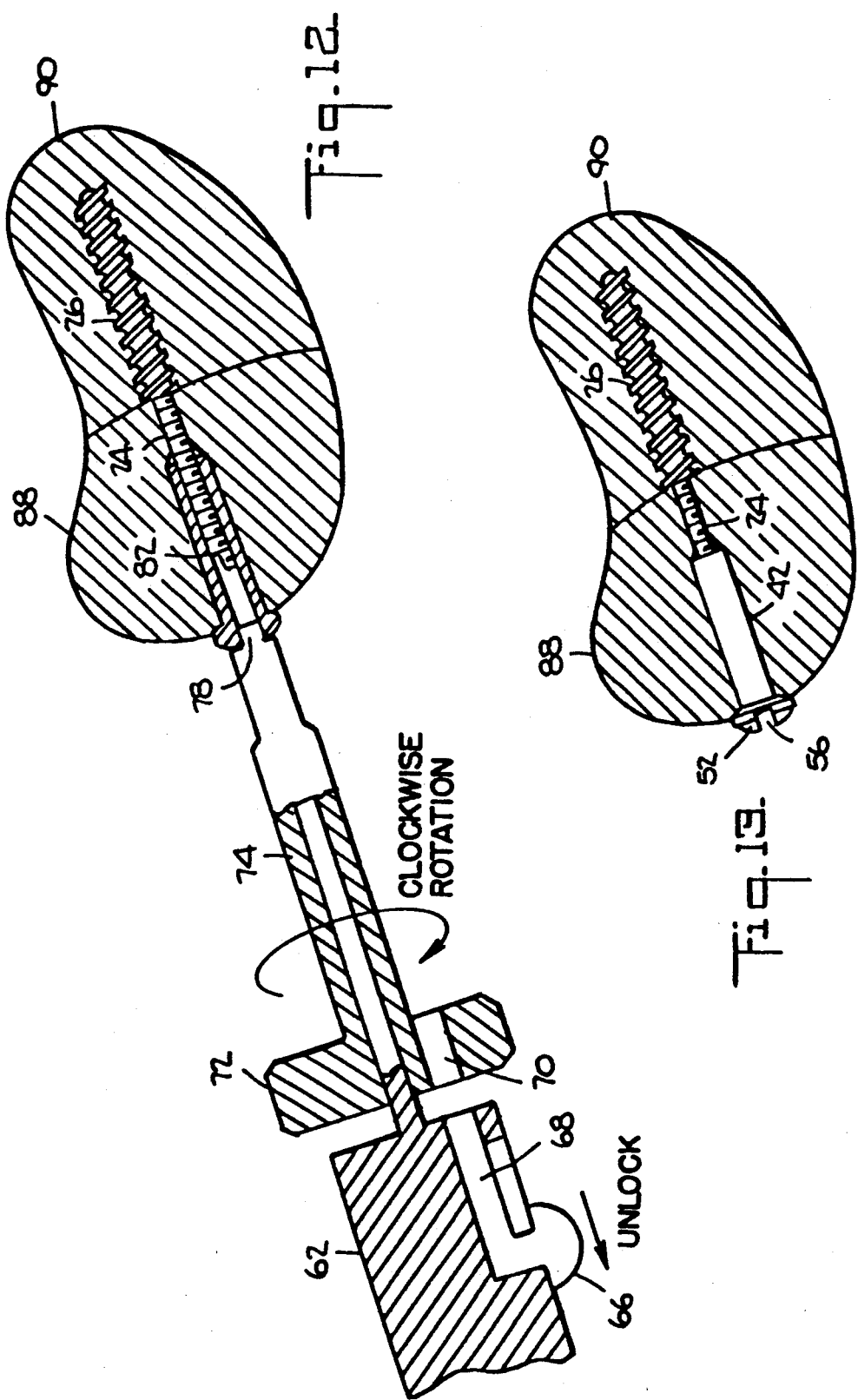

SCREW AND DRIVER

This invention relates generally to screws and drivers for those screws and relates more particularly to bone screws and specially adapted drivers therefor.

In the prior art, many types of screws have been known. More recently, in the field of orthopedics, various developments, have taken place. A number of these are described in an article by Raymond G. Tronzo, M.D. entitled "Hip Nails For All Occasions", *Orthopedic Clinics of North America* - Vol 5, No. 3, July 1974. However, despite these developments a continuing need exists for improvements in bone screws and for drivers for inserting those screws, in particular for bone screws that are useful for fractures in small bones.

An object of this invention is a bone screw which is versatile, easily implanted and removed, and useful alone or with plates and washers.

Another object of this invention is a driver specifically adapted for inserting the bone screw of the invention.

Other objects of this invention are a bone screw and driver combination and a method for using that combination.

SUMMARY OF THE INVENTION

These and other objects are satisfied by the bone screw implant of the invention which comprises a variable length implant comprising in a connected relationship:

(a) a threaded shank portion having a distal portion and a proximal portion, the proximal portion having a thread with a diameter d';

(b) a sleeve having a head with a diameter D (larger than d') and having an inner thread which threads with and can move longitudinally along the proximal portion of the threaded shank;

(c) a connector means which connects the sleeve with the proximal threaded shank portion but which permits the sleeve to move longitudinally along the proximal portion, resulting in a maximum and a minimum implant length.

Also, according to the invention, an implant comprises in a non-removably connected relationship: (a) a threaded shank portion having a specially adapted and specially shaped head having a diameter no larger than the diameter of the proximal portion of the threaded shank and (b) an internally threaded sleeve having an outer diameter only slightly larger than the diameter of the proximal portion of the threaded shank portion, the thread of the proximal portion of the threaded shank portion and the internal threading of the sleeve being adapted to thread with each other, the sleeve having a head (1) with a larger diameter than the diameter of the main body of the sleeve and (2) with a recess into which a driver means can be placed so as to thread or unthread the sleeve onto or from the proximal portion of the threaded shank portion of the implant.

Also according to the invention, a driver especially suitable for inserting and removing the implant of the invention comprises:

(a) a handle;

(b) an inner rod having at its distal end a first driver means which fits within the sleeve of the implant and mates with the proximal end of the threaded shank portion of the implant, the inner rod being connected at its proximal end to the handle;

(c) an outer cylindrical portion having a locking means at its proximal end adapted for locking the outer cylindrical portion with the handle when desired and the outer cylindrical portion having at its distal end a second driver means which mates with the recess in the head of the sleeve of the implant of the invention.

Also according to the invention a method of compressing a fracture in a bone comprises:

(a) drilling a hole into and through the proximal side of the fracture and into the distal side of the fracture;

(b) "overdrilling" the proximal side of the fracture (i.e., drilling the same hole with a drill bit which is large enough to the accommodate shaft of the sleeve;

(c) with the implant of the invention extended to its maximum length, placing the driver of the invention (when in its locked position) so that the first driver means located on the inner rod and preferably also the second driver means are engaged with the implant and contact the proximal end of the threaded shaft portion of the implant and the head of the sleeve, respectively, and then rotating the handle so as to insert the implant according to the invention into and through the proximal portion of the fractured bone and into the distal portion of the fractured bone; and (d) unlocking the driver of the invention, holding the inner rod of the driver steady (which holds the threaded shank steady), and then rotating the outer cylinder clockwise so that the implant has a length which is shorter than its maximum length and so that the fracture is compressed.

BRIEF DESCRIPTION OF THE DRAWINGS

FIG. 1 is an exploded view of an embodiment of the implant of the invention, showing the threaded shaft portion separated from the sleeve before it is non-removably connected to the sleeve, with the sleeve shown partially in cross-section.

FIG. 2 is a pictorial representation of the device of FIG. 1, with the sleeve and the threaded shaft portion nonremovably connected together.

FIG. 3 is a magnified view of the device shown in FIG. 2, but with the sleeve portion of the device shown partially in cross-section.

FIG. 4 is a cross-sectional view taken along the lines 4—4 in FIG. 2.

FIG. 5 is a pictorial representation of an embodiment of the driver of the invention, showing the locking means located on the handle of the device which locks into a preferably knurled portion of the outer cylindrical portion, the outer cylindrical portion having a special driver means at its distal end, and showing the inner rod portion having another special driver means at its distal end. When the knob is moved toward the tip of the screw driver, the driver goes from its unlocked to its locked position.

FIG. 6 is a view partially in cross-section of the driver shown in FIG. 5 (with the driver in its locked position).

FIG. 7 is a pictorial representation showing (with use of inner phantom lines) the driver means located at the distal end of the inner rod of the driver just prior to its contacting the proximal end of the threaded shank portion of the implant of the invention, at a point in time when the implant of the invention has its maximum length.

FIG. 8 is an end view of FIG. 3 (viewed along lines 8—8 in FIG. 3).

FIG. 9 is a pictorial representation in cross-section illustrating the first step in the method of inserting the implant of the invention into a fractured bone, a drill bit shown drilling a hole into and through the proximal portion of the fracture and into the distal portion of the fracture.

FIG. 10 is a pictorial representation in cross-section illustrating the second step in the method of inserting the implant of the invention, a second drill bit having a larger diameter than that shown in FIG. 9 being used to "overdrill" (i.e., to accommodate the shaft of the sleeve) the proximal portion of the fracture.

FIG. 11 is a pictorial representation in cross-section showing the distal portion of the threaded shank portion of the implant being inserted into the distal portion of the fracture by means of the driver means on the distal end of the inner rod of the driver (preferably together with the driver means on the distal end of the cylinder), these two driver means being mated with recesses in the implant, prior to the sleeve being threaded down onto the proximal portion of the threaded shank portion of the implant of the invention (the fracture being at this time not compressed). The driver of the invention at this time is in its locked position.

FIG. 12 is a pictorial representation (partially in cross-section) showing the driver in its unlocked position with the driver means located at the distal end of the inner rod positioned adjacent to and engaged with the proximal end of the threaded shank portion and with the driver means located at the distal end of the outer cylindrical portion being located adjacent to and engaged with the recess in the head of the sleeve portion of the implant of the device of the invention. An arrow indicates the clockwise direction in which the driver will be turned so as to insert the implant of the invention.

FIG. 13 is a pictorial representation of the implant of the invention after it has been fully inserted into a fracture and after the fracture has been compressed by the implant and after the driver has been removed.

DETAILED DESCRIPTION OF THE INVENTION

In FIG. 1, showing a preferred embodiment of the implant 20 of the invention prior to the time when the parts of the implant 20 are assembled together, a threaded shank portion 22 comprises a proximal threaded shank portion 24 and a distal threaded shank portion 26. In the embodiment shown in FIG. 1, the threads of proximal threaded shank portion 24 and distal threaded shank portion 26 are not identical, but rather are of different diameters, pitches, and profiles. This is preferred but is not required. The directions of the threads in this embodiment are the same (both preferably are the same and both preferably are right-handed). In the embodiment shown in FIG. 1, the length of the proximal threaded shank portion 24 (preferably machine thread) is slightly shorter than the length of the distal threaded shank portion 26 (preferably bone thread). These relative lengths can be modified as desired, depending upon the intended use. The diameter 32 of the proximal threaded shank portion 24 is slightly smaller than the diameter 34 of the distal threaded shank portion 26. At the proximal end 36 of proximal threaded shank portion 24 a cutout 38 is present and in a preferred embodiment is half-cylindrical. The cutout 38 can (if desired) have a rounded boundary 40. For clarity, sleeve 42 is shown separated from threaded shank portion 22, but this is at a time prior to the assembly of the implant of the invention. Sleeve 42 has an outer diameter 44 and an inner diameter 46. Sleeve 42 has internal threading 48 which mates with and threads with threading 25 of proximal threaded shank portion 24. Sleeve 42 has an outer surface 50 which is substantially smooth. At the proximal end of sleeve 42 is a head 52 which is integral with sleeve 42. Head 52 has an outer diameter 54 and has a recess 56 therein. Recess 56 is preferably in the shape of a slot but can be, if desired, of other shapes, for example, hexagonal. Outer diameter 54 will be larger than the diameter drilled in the proximal portion of the bone fracture during "overdrilling".

The length 28 of proximal threaded shaft 24 should be no longer than the length of the sleeve 42 without including the length of head 52. The number of threads in internal threading 48 should be the minimum number of threads to function properly as a machine thread. And the hole 58 should be located just proximal to the last thread in internal threading 48.

In FIG. 2, sleeve 42 is shown partially threaded down onto proximal threaded shank portion 24. Proximal threaded shank portion 24 and distal threaded shank portion 26 are integral with each other. In FIG. 2, a hole 58 in sleeve 42 is shown. Prior to assembly of the implant 20, a hole 58 is drilled into sleeve 42. After the sleeve 42 is assembled together with the threaded shank portion 22, the threaded shank portion 22 and the sleeve 42 are nonremovably connected together when manufactured by any suitable means, for example, by deforming some of the threads 25 through hole 58 so that sleeve 42 cannot become disengaged from threaded shank portion 22. Another alternative is to deform proximal end 36 so as to prevent disengagement of sleeve 42 from threaded shank portion 22.

In FIG. 3, shown is a magnified view of the device of FIG. 2, with a portion of sleeve 52 shown in cross-section. Cutout 38 is located at the proximal end 36 of proximal thread shaft portion 24, and hole 58 is located in sleeve 42. Proximal threaded shaft portion 24 is threaded within and engaged with internal threading 48 of sleeve 42.

In FIG. 4, taken along the lines 4—4 in FIG. 2, proximal threaded shank portion 24 is threadably engaged within internal threading 48 of sleeve 42. Areas 59 are multiple areas of deformed threads which prevent future disengagement of the device.

In FIG. 5 is shown a driver which is especially suitable for inserting and removing the implant of the invention.

Driver 60 has a handle 62, which is fixedly attached to an inner rod 64. Handle 62 has a slidable portion 66, which can be in the shape of any of a variety of structures, for example (as shown) a knurled portion of a cylinder or a knob. When slidable portion 66 is slid to its distal-most position within handle 62, a small rod 68 fixed thereto can be positioned so that it fits into one of a multiplicity of holes 70 in (preferably) knurled cylindrical portion 72. Knurled cylindrical portion 72 is integral with outer cylindrical portion 74, which fits over inner rod 64 and which has located at its distal-most end 76 a tab 78 for mating with the recess 56 in the head 52 of the sleeve 42. Outer cylindrical portion 74 can be in a locked position, wherein small rod 68 is locked within a hole 70. Outer cylindrical portion 74 can alternatively be in an unlocked position, wherein slidable portion 66 is retracted in a proximal direction so that small rod 68 is not engaged within a hole 70.

Tab 78 is integral with distal-most end 76 of outer cylindrical portion 74. Locking mechanism 78 is shaped so that it can mate with recess 56 in head 52.

The distal-most end 82 of inner rod 64 is shaped so that it can mate and engage with cutout 38 at proximal end 36 of proximal threaded shank portion 24.

Outer cylindrical portion 74 can have at least two integrally attached portions having different diameters 84, 86, if desired; or alternatively, it can have one diameter throughout, which is integrally attached to preferably knurled cylindrical portion 72. Preferably, also, knurled cylindrical portion 72 has a multiplicity of holes 70 therein, into any one of which rod 68 can be engaged.

In FIG. 8, an end view taken along the lines 8—8 in FIG. 3 shows head 52 of sleeve 42 with recess 56 therein and shows also proximal threaded shank portion 24 having proximal end 36 and cutout 38 (which is preferably in the shape of a half-cylinder) therein.

In FIG. 9, a proximal portion 88 of a fractured bone and a distal portion 90 of that bone are shown separated from each other. A hole is drilled into and through the proximal portion of the fractured bone and into the distal portion of the bone by a drill bit 92.

In FIG. 10, a larger diameter drill bit 94 is illustrated within that same bone so as to enlarge the hole in the proximal portion of that fractured bone thereby "overdrilling" the proximal portion of that bone to accommodate the shaft 42 of the sleeve.

As illustrated in FIG. 11, with the implant 20 in its fully extended position so that it has its longest possible length, the distal threaded shank portion 26 of the implant 20 is inserted into the distal portion 90 of the fracture and into its optimal position in the bone. The distal-most end 82 of inner rod 64 is shown engaged with the end 36 and cutout 38 of proximal threaded shank portion 24. Tab 78 meshes with and engages with recess 56 within head 52.

In FIG. 12, slidable portion 66 is retracted so that it is at its proximal-most position, small rod 68 (attached thereto) is retracted from hole 70, and knurled cylindrical portion 72 is now free to rotate. When knurled cylindrical portion 72 is rotated in a clockwise direction as indicated, the sleeve 42 of the implant 20 advances so as to shorten the overall length of the implant 30 and so as thereby to compress the fracture as force is exerted by head 54 down onto bone where head 54 contacts the bone.

As shown in FIG. 13, with the driver 60 removed, the implant 20 can be allowed to remain within the bone as desired. If its removal is desired, the driver 60 especially suitable for inserting the implant can be profitably used for removing the implant. In this event, the reverse of the procedure just described is used, with the distal-most end 82 of inner rod 64 being positioned to abut against and engage with proximal end 36 of proximal threaded shank portion 24 and with cutout 38 and (at the same time) such that locking mechanism 78 abuts against and engages with recess 56 in head 52 of sleeve 42 of implant 20. The driver 60 is at this time in its unlocked position and knurled cylindrical portion 72 is rotated in a clockwise or counter-clockwise direction to line up the nearest hole 70 with the rod 68. The screwdriver is then locked and turned as a unit counterclockwise to remove the screw.

Because the implant of the invention comprises a special threaded shank portion and a special internally threaded sleeve portion, which parts are connected together in a non-removable relationship, an implant having many advantages results. The implant can be easily inserted as a one-piece device, without the need for assembling any parts together during surgery. Likewise, the device can be easily unscrewed and removed. The slot (or other suitable shape) in the head of the sleeve, together with the feature of the specially shaped proximal end of the threaded shank portion of the implant which fits within the sleeve, results in the advantages that the threaded shaft portion can be held stationary while the screw is being shortened, causing bone compression. The device can be made in a variety of sizes so that it can be used to repair fractures of the small bones of the hand and foot (including diaphaseal, metaphysal, epiphyseal and articular). The device can be used for arthrodesis of small bones, for repair of avulsion fractures of the knee, elbow, shoulder, or any joint with tendenous attachment injury, or for lagging fracture fragments of long bones. The device is especially suitable for use as a small lag screw and reduction device.

The implant can be used either alone or with plates and washers, and the implant generates bone compression by itself.

The driver of the invention which is especially suitable for inserting and removing the implant of the invention has also several advantages. The first driver means located on the inner rod fits securely within the sleeve of the implant and mates with the proximal end of the threaded shank portion of the implant, so as to enable the threaded shank portion of the implant to be inserted into and through the proximal side of the fracture and into the distal side of the fracture and also enables the driver to prevent slippage of the driver while the outer cylindrical portion of the driver having a second driver means is used to thread the sleeve onto the implant so as to compress the fracture. That is, both the functions of inserting the screw and then lagging the fracture are accomplished by the same implant.

We claim:

1. A variable length implant comprising in a connected relationship:
   (a) a threaded shank having:
   (1) a distal threaded shank portion having a distal end and
   (2) a proximal threaded shank portion having a proximal end and having threading with a diameter d', said proximal threaded shank portion having located at said proximal end thereof a means for inserting said implant,
   (b) a sleeve having a head with a diameter D (larger than d') and having a distal end and a proximal end and having an inner threading which threads with said proximal threaded shank portion, resulting in an implant having a maximum implant length and a minimum implant length, said proximal end of said sleeve having a means for compressing said implant, and said means for inserting said implant fitting within said means from compressing said implant; and
   (c) a connector means which connects said sleeve near said distal end of said sleeve with said proximal threaded shank portion near said proximal end of said proximal threaded shank portion but which permits said sleeve to move longitudinally with respect to said distal threaded shank portion after said maximum implant length is reached, said connector means comprising a hole in said sleeve through which thread in said proximal threaded shank portion has been deformed.

2. An implant according to claim 1, wherein said connector mean is a projection which when deformed interferes with disengagement of said sleeve from said threaded shank.

3. A method of comprising a fractured bone having a proximal bone portion and a distal bone portion with a variable length implant having a threaded shank with a proximal threaded portion with a diameter d' and a distal threaded portion, a sleeve having a head with a diameter D larger than d' and having a distal end and proximal end and having a threaded bore which threads with said proximal threaded shank portion resulting in an implant having a maximum implant length and a minimum implant length, and a connector means connecting said sleeve near the distal end thereof with a proximal end of the proximal threaded shank portion but which permits said sleeve to move longitudinally with respect to said distal threaded shank portion after said maximum implant length is reached, said method comprising;
(a) drilling a hole into and through said proximal bone portion and into said distal bone portion;
(b) "overdrilling" said proximal bone portion with a drill bit having a diameter b which is large enough to accommodate the shaft of the implant sleeve;
(c) when said implant is at its maximum length, inserting said implant into and through said proximal bone portion and into said distal bone portion;
(d) tightening down said sleeve of said implant onto said proximal threaded shank portion of said implant so as to shorten the overall length of said screw so that said implant has a length shorter than its maximum length, thereby compressing said fracture by use of said implant.

4. A driver and implant combination comprising:
1) a variable length implant comprising in a connected relationship:
(a) a threaded shank having:
(1) a distal threaded shank portion having a distal end and
(2) a proximal threaded shank portion having a proximal end and having threading with a diameter d';
(b) a sleeve having a head with a diameter D (larger than d') and having a distal end and a proximal end and having an inner threading which threads with said proximal threaded shaft portion, resulting in an implant having a maximum implant length and a minimum implant length; and
(c) a connector means which connects said sleeve near said distal end of said sleeve with said proximal threaded shank portion near said proximal end of said proximal threaded shaft portion but which permits said sleeve to move longitudinally with respect to said distal threaded shaft portion after said maximum implant length is reached, in combination with
2) a driver for inserting and removing an implant having a threaded shank portion which threads with a sleeve having a head, said driver comprising:
(a) a handle;

5. A variable length implant comprising in a connected relationship:
(a) a threaded shank having:
(1) a distal threaded shank portion having a distal end and
(2) a proximal threaded shank portion having a proximal end and having threading with a diameter d', said proximal threaded shank portion having located at said proximal end thereof a means for inserting said implant;
(b) a sleeve having a head with a diameter D (larger than d') and having a distal end and a proximal end and having an inner threading which threads with said proximal threaded shank, portion resulting in an implant having a maximum implant length and a minimum implant length, said proximal end of said sleeve having a means for compressing said implant and said means for inserting said implant fitting within said means for compressing said implant;
(c) a connector means which connects said sleeve near said distal end of said sleeve with said proximal threaded shank portion near said proximal end of said proximal threaded shank portion but which permits said sleeve to move longitudinally with respect to said distal threaded shank portion after said maximum implant length is reached; and
(d) a means for stopping said sleeve when said minimum displacement is reached so that said distal threaded shank portion and said proximal threaded shank portion are separated from each other by said means for stopping said sleeve.

6. A variable length implant comprising in a connected relationship:
(a) a threaded shank having:
(1) a distal threaded shank portion having a distal end and
(2) a proximal threaded shank portion having a proximal end and having threading with a diameter d', said proximal threaded shank portion having located at said proximal end thereof a means for inserting said implant;
(b) a sleeve having a head with a diameter D (larger than d') and having a distal end and a proximal end and having an inner threading which threads with said proximal threaded shank portion, resulting in an implant having a maximum implant length and a minimum implant length, said proximal end of said sleeve having a means for compressing said implant, and said means for inserting said implant fitting within said means for compressing said implant;
(c) a connector means which connects said sleeve near said distal end of said sleeve with said proximal threaded shank portion near said proximal end of said proximal threaded shank portion but which permits said sleeve to move longitudinally with respect to said distal threaded shank portion after said maximum implant length is reached; and
(d) a means for stopping said sleeve when said minimum displacement is reached, said distal threaded shank portion having a diameter A and said proximal threaded shank portion having a diameter B, wherein A is greater than B and wherein said means for stopping said sleeve has a diameter greater than B.

* * * * *